US008623272B2

(12) United States Patent
Prasad et al.

(10) Patent No.: US 8,623,272 B2
(45) Date of Patent: *Jan. 7, 2014

(54) NON-MAGNETIC COBALT-PALLADIUM DENTAL ALLOY

(75) Inventors: Arun Prasad, Cheshire, CT (US); Paul J. Cascone, Del Mar, CA (US)

(73) Assignee: The Argen Corporation, San Diego, CA (US)

( * ) Notice: Subject to any disclaimer, the term of this patent is extended or adjusted under 35 U.S.C. 154(b) by 906 days.

This patent is subject to a terminal disclaimer.

(21) Appl. No.: 12/050,006

(22) Filed: Mar. 17, 2008

(65) Prior Publication Data

US 2008/0232998 A1 Sep. 25, 2008

Related U.S. Application Data

(60) Provisional application No. 60/896,182, filed on Mar. 21, 2007, provisional application No. 60/941,908, filed on Jun. 4, 2007, provisional application No. 60/978,828, filed on Oct. 10, 2007.

(51) Int. Cl.
  *C22C 19/07* (2006.01)
  *C22C 30/00* (2006.01)

(52) U.S. Cl.
  USPC ............................................ 420/436; 420/588

(58) Field of Classification Search
  USPC .................................. 420/436, 588; 148/425
  See application file for complete search history.

(56) References Cited

U.S. PATENT DOCUMENTS

| | | | |
|---|---|---|---|
| 2,226,079 A | 12/1940 | Spanner | |
| 2,890,114 A | 6/1959 | Ruthardt et al. | |
| 2,946,679 A | 7/1960 | Darling | |
| 3,134,671 A | 5/1964 | Prosen | |
| 3,141,765 A * | 7/1964 | Brown et al. | 75/364 |
| 3,155,467 A | 11/1964 | Yamamoto et al. | |
| 3,764,493 A * | 10/1973 | Nicks et al. | 205/370 |
| 3,928,913 A | 12/1975 | Schaffer | |
| 4,098,605 A | 7/1978 | Nepela et al. | |
| 4,195,988 A | 4/1980 | Ito | |
| 4,201,577 A | 5/1980 | Ingersoll et al. | |
| 4,253,869 A | 3/1981 | Prosen | |
| 4,255,190 A | 3/1981 | Prosen | |
| 4,382,909 A | 5/1983 | Zwingmann | |
| 4,387,072 A | 6/1983 | Schaffer | |
| 4,459,263 A | 7/1984 | Prasad | |
| 4,681,735 A | 7/1987 | Groll et al. | |
| 4,735,772 A | 4/1988 | van der Zel | |
| 4,917,861 A | 4/1990 | Schaffer et al. | |
| 5,236,789 A | 8/1993 | Cowie et al. | |
| 5,799,386 A | 9/1998 | Ingersoll et al. | |
| 5,916,518 A | 6/1999 | Chesnes | |
| 6,365,285 B1 | 4/2002 | Chesnes | |
| 6,554,920 B1 | 4/2003 | Jackson et al. | |
| 6,613,275 B1 | 9/2003 | Vuilleme | |
| 6,656,420 B2 | 12/2003 | Prasad et al. | |
| 6,756,012 B2 | 6/2004 | Prasad | |
| 7,569,116 B2 | 8/2009 | Ono et al. | |
| 7,794,652 B2 * | 9/2010 | Cascone | 420/436 |
| 2006/0147334 A1 | 7/2006 | Cascone | |
| 2008/0070058 A1 | 3/2008 | Dasgupta et al. | |
| 2008/0070192 A1 | 3/2008 | Dasgupta et al. | |
| 2011/0275033 A1 | 11/2011 | Dasgupta et al. | |
| 2012/0244035 A1 | 9/2012 | Cascone et al. | |

FOREIGN PATENT DOCUMENTS

| | | | |
|---|---|---|---|
| DE | 10136997.2 | 7/2001 | |
| EP | 1595523 A1 | 11/2005 | |
| EP | 1900836 A1 | 3/2008 | |
| GB | 2 421 513 | * 6/2006 | ............. C22C 19/07 |
| JP | 56-189769 | 7/1983 | |
| WO | WO 2007/042841 | 4/2007 | |

OTHER PUBLICATIONS

Kinouchi et al., "Pd-Co Dental Casting Ferromagnetic Alloys", J Dent Res, Jan. 1981, vol. 60, No. 1, pp. 50-58.
International Search Report for International Application PCT/US2008/057253, filed Mar. 17, 2008, Report completed May 30, 2008, mailed Jul. 31, 2008, 2 pgs.

* cited by examiner

*Primary Examiner* — Jessee Roe
(74) *Attorney, Agent, or Firm* — Knobbe Martens Olson & Bear LLP

(57) ABSTRACT

A non-magnetic cobalt based "noble" metal dental alloy is provided. The alloy generally contains at least 25 wt. % palladium, from 15 to 30 wt. % chromium and a balance of cobalt, where to ensure the alloy is non-magnetic the concentration of chromium in the alloy is at least 20 wt. %, or if the concentration of chromium is less than 20 wt. % the combined concentration of chromium, molybdenum, tungsten, niobium, tantalum vanadium and rhenium is greater than 20 wt. %.

16 Claims, 1 Drawing Sheet

TABLE 3: EXEMPLARY ALLOY COMPOSITIONS

| # | Vickers Hardness Avg. | Tensile Test | | | | Melting Range | | Thermal Expansion Coefficient | | Composition (wt%) | | | | | | | Ion Release μg/cm² (7 day) |
|---|---|---|---|---|---|---|---|---|---|---|---|---|---|---|---|---|---|
| | | Yield, Kpsi (0.2% offset) | UTS, Kpsi | Mod Mpsi | EL% | Solidus (°C) | Liquidus (°C) | 25-500°C (10⁻⁶) | 25-600°C (10⁻⁶) | Co | Cr | Pd | Mo | W | X | |
| 1 | 341 | N/D | N/D | N/D | N/D | 1286 | 1358 | 15.1 | 15.6 | 55 | 20 | 25 | - | - | - | 86.8 |
| 2 | 334 | N/D | N/D | N/D | N/D | 1140 | 1358 | 14.2 | 14.3 | 50 | 20 | 25 | - | - | 5 Ga | 67 |
| 3 | 370 | N/D | N/D | N/D | N/D | 1278 | 1345 | 15.4 | 15.8 | 50 | 25 | 25 | - | - | - | 61.1 |
| 4 | 382 | N/D | N/D | N/D | N/D | 1115 | 1351 | 14.2 | 14.4 | 45 | 25 | 25 | - | - | 5 Ga | 65.6 |
| 5 | 405 | N/D | N/D | N/D | N/D | 1126 | 1349 | 15.7 | 16.1 | 50 | 22.5 | 25 | - | - | 2.5 Ga | 64.1 |
| 6 | 287 | N/D | N/D | N/D | N/D | 1280 | 1342 | 17.2 | 17.6 | 45 | 20 | 25 | - | - | - | 40.6 |
| 7 | 341 | N/D | N/D | N/D | N/D | 1283 | 1333 | 16.9 | 17.5 | 40 | 25 | 25 | - | 10 | - | 3.2 |
| 8 | 339 | N/D | N/D | N/D | N/D | 1270 | 1308 | 14.6 | 15.2 | 40 | 25 | 25 | 3.5 | 10 | - | 11 |
| 9 | 340.8 | N/D | N/D | N/D | N/D | 1285 | 1330 | 16.7 | 17.8 | 50 | 25 | 25 | - | 5.5 | 1 Si | N/D |
| 10 | 319.1 | N/D | N/D | N/D | N/D | 1280 | 1328 | 15.4 | 16.7 | 45 | 25 | 25 | 5 | - | - | N/D |
| 11 | 289.3 | 84.6 | 86.9 | 28.3 | 5 | 1265 | 1303 | 15.3 | 15.7 | 40 | 25 | 25 | 10 | - | - | N/D |
| 12 | 333 | N/D | N/D | N/D | N/D | 1278 | 1336 | 15.8 | 16.9 | 45 | 30 | 25 | - | - | - | N/D |
| 13 | 303.2 | N/D | N/D | N/D | N/D | 1268 | 1312 | 15.6 | 16.1 | 40 | 30 | 25 | 5 | - | - | N/D |
| 14 | 404.7 | N/D | N/D | N/D | N/D | 1255 | 1288 | 14.7 | 15.3 | 35 | 30 | 25 | 10 | - | - | N/D |
| 15* | 283 | 72.1 | 86.4 | 26.3 | 14 | 1287 | 1326 | 15.2 | 15.6 | 55 | 15 | 25 | 5 | - | - | N/D |
| 16 | 307 | 81 | 102.8 | 29.4 | 18 | 1285 | 1330 | 15 | 15.1 | 50 | 20 | 25 | 5 | - | - | N/D |
| 17 | 292 | 76.4 | 106.8 | 25.5 | 28 | 1284 | 1320 | 15.3 | 15.9 | 50 | 15 | 25 | 10 | - | - | N/D |
| 18 | 300 | 79.1 | 103.9 | 27.5 | 18 | 1271 | 1310 | 14.8 | 15.3 | 45 | 20 | 25 | 10 | - | - | N/D |
| 19 | 298 | 82.5 | 111.1 | 23.4 | 18 | 1295 | 1328 | 15.6 | 16 | 50 | 17.5 | 25 | 7.5 | - | 0.5 Si | N/D |
| 20 | 331 | 98.8 | 108.4 | 29.3 | 4 | 1238 | 1321 | 15.7 | 16.1 | 49.5 | 17.5 | 25 | 7.5 | - | - | N/D |
| 21 | 361 | 97.4 | 122.5 | 29.9 | 4 | 1186 | 1286 | 15 | 15.6 | 40 | 20 | 25 | 15 | - | - | N/D |
| 22 | 335 | 90.1 | 99.8 | 27.9 | 4 | 1252 | 1287 | 14.4 | 14.8 | 44.75 | 20 | 25 | 10 | - | .25 B | 4.7 |
| 23 | 411.6 | N/D | N/D | N/D | N/D | 1173 | 1225 | 15 | 15.3 | 49.5 | 15 | 25 | 10 | - | 0.5 B | N/D |
| 24 | 437 | N/D | N/D | N/D | N/D | 1191 | 1241 | 13.9 | 14.3 | 44.5 | 15 | 25 | 15 | - | 0.5 B | N/D |
| 25 | 462.6 | N/D | N/D | N/D | N/D | 1182 | 1247 | 13.4 | 13.8 | 39.75 | 15 | 25 | 20 | - | 0.25 B | N/D |
| 26 | 339.6 | N/D | N/D | N/D | N/D | 1234 | 1272 | 13.7 | 14.2 | 39.75 | 20 | 25 | 15 | - | 0.25 Si | N/D |
| 27 | 415 | N/D | N/D | N/D | N/D | 1185 | 1230 | 14.8 | 15.2 | 39.75 | 20 | 25 | 15 | - | 0.25 B | N/D |
| 28 | 460.3 | N/D | N/D | N/D | N/D | 1247 | 1279 | 14.4 | 14.8 | 39.75 | 20 | 25 | 15 | - | 0.25 Ge | N/D |
| 29 | 422 | N/D | N/D | N/D | N/D | 1254 | 1287 | 14.5 | 14.9 | 39.75 | 20 | 25 | 15 | - | 0.25 Al | N/D |
| 30 | 326 | N/D | N/D | N/D | N/D | 1253 | 1283 | 13.7 | 14.2 | 39.75 | 20 | 25 | 15 | - | 0.25 Ce | N/D |
| 31 | 365.6 | 92.6 | 120.7 | 23.9 | 3 | N/D | N/D | 14.2 | 14.8 | 42.75 | 20 | 25 | 12 | - | 0.25 B | N/D |

* Alloy Exhibited Magnetic Properties, "N/D" = no data, "-" = 0 wt% in alloy

NON-MAGNETIC COBALT-PALLADIUM DENTAL ALLOY

CROSS-REFERENCE TO RELATED APPLICATIONS

The current application claims priority to U.S. Provisional Application No. 60/896,182, filed Mar. 21, 2007, U.S. Provisional Application No. 60/941,908, filed Jun. 4, 2007, and U.S. Provisional Application No. 60/978,828, filed Oct. 10, 2007, the disclosures of which are incorporated herein by reference.

FIELD OF THE INVENTION

The current invention is directed to an improved dental alloy, and more specifically to a non-magnetic cobalt based dental alloy containing at least 25% palladium, and where the combined concentration of chromium, molybdenum, tungsten, niobium, tantalum and rhenium is sufficient to ensure a non-magnetic material.

The current invention is also directed to an improved dental alloy, and more specifically to a non-magnetic cobalt based dental alloy containing at least 25% gold plus platinum group elements with the majority of the 25% addition consisting of palladium.

BACKGROUND OF THE INVENTION

Dental alloys employed in the porcelain-fused-to-metal processing technique may be classified into several groups, including gold based, palladium based, cobalt based, and titanium based. One of the most important criteria in deciding which alloy to use is the cost of the alloy. The cost of the alloy is dependent upon the commodity prices of the alloy components. For example, in March 2007, the cost of the major components of each the above alloys was:

Gold $730 per Troy ounce,
Palladium $350 per Troy ounce, and
Cobalt $2.23 per Troy ounce.

The economic advantage of the base metal cobalt is obvious, but the functional characteristics of base metal alloys do not compare with those of gold based or palladium based alloys, and for this reason they are not generally used in dental products. For example, in general cobalt base metal alloys are more difficult to cast, grind and bond to porcelain.

There have been numerous attempts to improve the functional characteristics of cobalt based alloys through the addition of gold and the platinum group metals (the platinum group metals consist of platinum, palladium, rhodium, iridium, osmium and ruthenium). Examples from the prior art are listed in Table 1, below.

TABLE 1

SUMMARY OF PRIOR ART

| Author | US Pat. # | Comments |
|---|---|---|
| Prosen | 4,253,869 | Describes a cobalt chromium alloy with 7 to 15 wt. % ruthenium. |
| Prosen | 4,255,190 | Describes a cobalt chromium alloy with 7 to 15 wt. % ruthenium with gallium. |
| Zwingmann | 4,382,909 | Describes a cobalt chromium alloy that with 1 to 70 wt. % palladium. |
| Prasad | 4,459,263 | Describes a cobalt chromium alloy with 5 to 15 wt. % ruthenium. |
| Vuilleme | 6,613,275 | Describes a cobalt chromium alloy with 0.5 to 4 wt. % gold. |
| Prasad | 6,656,420 | Describes an alloy with 25 to 60 wt. % gold and up to 2 wt. % ruthenium balance cobalt. |
| Prasad | 6,756,012 | Describes a cobalt chromium alloy with up to 20 wt. % platinum or palladium, up to 10 wt. % gold and up to 6 wt. % ruthenium. |

In each case, some improvement in the functional characteristics of the base metal alloy has been achieved through the addition of gold and/or the platinum group metals. However, to date no successful commercial formulation of a cobalt based high palladium content alloy has been obtained that is consistent with the American Dental Association (ADA) guidelines for "noble" alloys required for use in dental products (i.e. alloys having at least 25% gold or palladium).

For example, although the Zwingmann patent discloses a wide range of possible cobalt based palladium alloys, most of these have strong magnetic properties. Likewise, Ivoclar Vivadent, Inc. manufactures a cobalt based high palladium content alloy sold under the tradename Calisto CP, which has a composition of 56 wt. % cobalt, 10 wt. % chromium, 26.2 wt. % palladium, 3 wt. % tungsten and 2 wt. % gallium. However, this alloy is also strongly magnetic and therefore poses potential problems for use in dental applications. Specifically, magnetic dental inserts and appliances can make it difficult if not impossible to use advanced imaging techniques such as Magnetic Resonance Imaging (MRI) on patients. In addition, such magnetic materials can cause false positives when individuals are scanned during security check-ins (for example, at airports). Accordingly, a need exists for improved cobalt based "noble" dental alloys that possess non-magnetic properties.

SUMMARY OF THE INVENTION

The invention is directed to improved cobalt based palladium containing alloys that are rendered non-magnetic through the additions of higher concentrations of other alloying elements.

In one embodiment, an exemplary cobalt based alloy in accordance with the current invention has the following composition: at least 25 wt. % palladium and 15 to 30 wt. % chromium, where either at least 20 wt. % of the alloy must be formed of chromium, or if the concentration of chromium in the alloy is less than 20 wt. % then the total combination of additive materials selected from the group consisting of chromium, molybdenum, tungsten, niobium, tantalum, vanadium and rhenium must be greater than 20 wt. %. An alternative statement of this composition can take the form of the following equation:

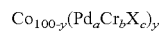

where X is a material selected from the group consisting of chromium, molybdenum, tungsten, niobium, tantalum, vanadium and rhenium; where y is at least 45 wt. %; and where a is at least 25 wt. %, b is from at least 15 wt. % to 30 wt. %, and c is dependent on the concentration of b in accordance with the following: where b is at least 20 wt. % then c is from 0 to 20 wt. %, and where b is less than 20 wt. % then the sum of b and c is greater than 20 wt. %. In an alternative of such an embodiment, y may range from at least 45 wt. % to 70 wt. %.

In another embodiment, an exemplary alloy in accordance with the current invention is formed having the following composition: cobalt 44.75 wt. %, chromium 20 wt. %, palladium 25 wt. %, molybdenum 10 wt. % and boron 0.25 wt. %.

In still another embodiment, the alloys in accordance with the current invention may be modified with gallium up to 2 wt. %, and/or silicon up to 3 wt. %, and/or boron up to 1 wt. %, and/or aluminum up to 3 wt. %, and/or germanium up to 3 wt. %, and/or rare earth elements such as cerium up to 1 wt. %.

In yet another embodiment, the alloys in accordance with the current invention may include traces amounts of other compatible materials, such as, for example, nickel, iron and copper.

In still yet another embodiment, indium and tin may be used to substitute for other deoxidizing elements such as, for example, gallium and aluminum.

The alloys in accordance with the current invention may be cast and processed using standard dental laboratory equipment and materials. Furthermore, they are also suitable for use with newer CAD/CAM and powder metallurgical applications where no casting is required.

In one embodiment, an exemplary cobalt-chromium in accordance with the current invention has the following composition: 20 to 30 wt % chromium, at least 25 wt % from the group consisting of palladium, iridium, osmium, ruthenium, platinum, rhodium, and gold, where the majority of the 25% addition consists of palladium, and from 0 to 10% molybdenum. In a preferred embodiment, at least 24 wt % of the additive is palladium, the remaining materials making up no more than 1 wt % of the addition.

In another embodiment, an exemplary alloy in accordance with the current invention is formed having the following composition: cobalt 45 wt %, chromium 25 wt %, palladium 25 wt %, and gallium 5 wt %.

In still yet another embodiment, the alloy in accordance with the current invention is able to be cast and processed using standard dental laboratory equipment and materials.

In still yet another embodiment, the alloy in accordance with the current invention may be modified with gallium up to 5.0 wt % and/or silicon up to 3 wt % and/or boron up to 1 wt %.

In still yet another embodiment, the alloy in accordance with the current invention may be modified with additions of niobium or rhenium up to 5 wt %.

BRIEF DESCRIPTION OF THE FIGURES

The above-mentioned and other features of this invention and the manner of obtaining and using them will become more apparent, and will be best understood, by reference to the following description, taken in conjunction with the accompanying figures. The figures depict only typical embodiments of the invention and do not therefore limit its scope, wherein:

FIG. 1 provides a table (referenced hereinafter as Table 3) containing a listing of exemplary alloy compositions in accordance with the current invention and their properties, as well as alloy compositions outside of the compositional ranges of the current invention for comparison purposes.

DETAILED DESCRIPTION OF THE INVENTION

This invention provides a non-magnetic cobalt based dental alloy capable of meeting the ADA requirements for a "noble" alloy that comprises at least 25 wt. % palladium and an additive of at least 15 to 30 wt. % chromium, where either at least 20 wt. % of the alloy is chromium, or if the concentration of chromium is less than 20 wt. % then the total combination of additive materials selected from the group consisting of chromium, molybdenum, tungsten, niobium, tantalum, vanadium and rhenium must be greater than 20 wt. %.

This invention also describes a non-magnetic cobalt based dental alloy containing at least 25% gold plus platinum group elements with the majority of the 25% addition consisting of palladium capable of meeting the ADA requirements for a "Noble" alloy.

As used herein, the term "non-magnetic" refers to materials that possess only diamagnetic properties, that is, that demonstrate neither ferromagnetic nor paramagnetic properties.

The inclusion of at least 25 wt. % palladium in the cobalt based dental alloy of the current invention has both metallurgical and economic benefits. Consider the price of gold and the platinum group metals:

Rhodium $6,200 per Troy ounce,
Platinum $1,360 per Troy ounce,
Ruthenium $530 per Troy ounce,
Gold $730 per Troy ounce,
Iridium $450 per Troy ounce,
Osmium $400 per Troy ounce, and
Palladium $350 per Troy ounce.

Based on this pricing, palladium is by far the lowest costing element of the group so it is an economic advantage to utilize palladium in place of gold and other platinum group elements in the fabrication of a "noble" alloy.

From a metallurgical perspective, palladium and cobalt are completely soluble in each other. Palladium also substitutes for molybdenum, tungsten and chromium in cobalt based alloys, allowing for the use of lower chromium concentrations. Palladium is also very effective in lowering melting temperature, acts as an alloy strengthener, is a thermal expansion adjuster for the alloys, and improves the alloys' oxidation and corrosion resistance. However, thus far a non-magnetic cobalt based alloy containing at least 25 wt. % palladium has not been formulated that meets all of the requirements for use in dental products. In the current invention, a non-magnetic low chromium cobalt-palladium alloy has been formulated that meets the requirements for use in dental alloys. The alloy has the following general composition 15 to 30 wt. % chromium;
from 0 to 20 wt. % molybdenum and/or tungsten, tantalum, niobium, vanadium and rhenium;
at least 25 wt. % palladium; and
the remainder cobalt;
where to obtain the non-magnetic properties necessary for dental applications either the concentration of chromium must be at least 20 wt. % or the where the concentration of chromium is less than 20 wt. % then the combined concentration of chromium, molybdenum, tungsten, niobium, tantalum, vanadium and rhenium in the alloy must be greater than 20 wt. %.

Although not specified in the above formulation of the alloy, it should be understood that in a preferred embodiment the alloy contains a minimum concentration of cobalt of at least 30 wt. %.

The alloy may also include other additives to improve specific properties, such as the casting or grain refinement properties. These additional materials include gallium, silicon, boron, germanium, aluminum and cerium in concentrations of up to 5.0 wt. %. More specifically, the concentration compositional ranges of these additional materials are: gallium up to 2 wt. %, and/or silicon up to 3 wt. %, and/or boron up to 1 wt. %, and/or aluminum up to 3 wt. %, and/or germanium up to 3 wt. %, and/or cerium up to 1 wt. %.

In the current invention, a cobalt-chromium alloy has been formulated that meets the requirements for use in dental alloys. The alloy has the following general composition 20 to 30 wt % chromium;
at least 25 wt % from the group consisting of palladium, iridium, osmium, ruthenium, platinum, rhodium, and gold, where the majority of the 25% addition consisting of palladium;
0 to 10 wt % molybdenum; and
the remainder cobalt.

The alloy may also include other additives to improve specific properties, such as the casting or grain refinement properties. These additional materials include gallium up to 5.0 wt % and/or silicon up to 3 wt % and/or boron up to 1 wt % and niobium or rhenium up to 5 wt % and tungsten and up to 10% molybdenum.

In a preferred embodiment, at least 24 wt % of the additive is palladium.

Exemplary compositional ranges for alloys contain these additional additives are provided below:

Palladium 25%;
Cobalt 40 to 55%;
Chromium 20 to 30%;
Gallium 0 to 5%;
Tungsten 0 to 10%;
Molybdenum 0 to 10%; and
Silicon 0 to 1%.

The increased palladium content of about 25 wt % can in some embodiment reduce the need for large additions of molybdenum or tungsten. The gallium addition lowers the melting range so that the alloy may be cast with a gas-oxygen torch. The small silicon and boron additions can also be used to improve the alloy's castability. If the alloy is to be cast by induction heating then the melting range can be higher reducing the need for any of these additives.

One exemplary alloy in accordance with the current invention is formed having the following composition: cobalt 45 wt %, chromium 25 wt %, palladium 25 wt %, and gallium 5 wt %.

Exemplary compositional ranges for alloys contain these additional additives are provided in Table 2, below:

TABLE 2

EXEMPLARY ALLOY COMPOSITIONAL RANGES

| Element | Min | Best | Max |
|---|---|---|---|
| Co | bal | bal | bal |
| Cr | 15 | 20 | 30 |
| Pd | 25 | 25 | 30 |
| Mo and/or W, Ta, Nb, V, Re | 0 | 10 | 20 |
| Al | 0 | 0.5 | 3 |
| B | 0 | 0.25 | 1 |
| Ce | 0 | 0.25 | 1 |
| Ga | 0 | 1 | 5 |
| Ge | 0 | 1 | 3 |
| Si | 0 | 0.5 | 3 |

The palladium content of at least 25 wt. %, and palladium's general enabling effect, can in some embodiments reduce the need for large additions of other materials such as chromium, molybdenum, tungsten, etc. However, key to the current invention is the requirement that the material as formed be non-magnetic. The inventors of the current invention have discovered that alloying cobalt with palladium and chromium within certain weight percentages, and optionally with the addition of molybdenum, tungsten, niobium, tantalum, vanadium, rhenium or other suitable elements in specific amounts, renders these alloys nonmagnetic. Specifically, it has been discovered that where the alloy has a content of chromium of at least 20 wt. %, or where the alloy has a content of chromium of at least 15 wt. % and the combined concentration of chromium, molybdenum, tungsten, or other suitable additive materials is greater than 20 wt. %, a non-magnetic cobalt-palladium alloy may be reliably formed. The properties and compositions of exemplary alloys formed in accordance with the current invention, including an example outside the compositional ranges of the current invention for comparison, are provided in Table 3 in the attached figure.

As shown in Table 3, alloys formed in accordance with the present invention exhibit non-magnetic properties as previously discussed; however, they also exhibit a wide variety of other physical properties that make them particularly promising for use in dental applications. For example, the alloys show liquidus temperatures below 1400° C. (typically below 1350° C.), which makes them adaptable for use with all standard casting, molding and shaping processes, as well as with new non-casting procedures. In addition, the alloy compositions of the current invention can be ground using traditional dental laboratory grinding media, making the alloy suitable for use with newer CAD/CAM and powder metallurgical applications where no casting is required. Substrates or final restorations can be milled from blocks made from these alloys. As powders, these alloys can be used either to create three dimensional performs utilizing appropriate binders and then be sintered or directly be sintered/melted such as for example, with a laser, to create substrate or final restoratives. Exemplary disclosures of such processes can be found, for example, in U.S. Pat. Nos. 7,084,370 and 6,994,549, the disclosures of which are incorporated herein by reference. It should be understood that while some prior art laser sintering techniques specify a specific range of useable alloy particulate sizes, the alloys of the current invention are contemplated for use in laser sintering techniques over all possible particulate size ranges.

Also, as shown in Table 3, in addition to the improved castability of these materials, the alloys show a wide variety of thermal expansion coefficients, namely from about 13 to about $18 \times 10^{-6}$ (as measured from about 25 to 500° C.). Because of the wide range of thermal expansion coefficients accessible by these materials, they can be used with all standard porcelains on the marketplace, such as, for example, high fusing conventional porcelains that have thermal expansion coefficients from about 13 to $15 \times 10^{-6}$, and low fusing porcelains that have thermal expansion coefficients from about 15 to $16 \times 10^{-6}$.

In addition to the main components, as previously discussed the alloys of the current invention may also contain concentrations of other additives to improve specific properties. For example, small concentrations (up to ~5 wt. %) of gallium, silicon, boron, aluminum, germanium and cerium can serve to deoxidize, lower the melting range, and improve the castability of the alloys. Specifically, the addition of gallium can lower the melting range of the alloy so that the material can be cast with a gas-oxygen torch. Alternatively, small silicon and boron additions can also be used to improve the alloy's thermal expansion and castability. However, it should be understood that these additives are not essential to the practice of the current invention. For example, if the alloy is to be cast by induction heating, then the melting range can be higher eliminating the need for any of these additives. Regardless, based on its castability and non-magnetic properties, one particularly preferred non-magnetic alloy in accordance with the current invention is formed having the following composition: cobalt 44.75 wt. %, chromium 20 wt. %, molybdenum 10 wt. %, palladium 25 wt. %, and boron 0.25 wt. %.

It is appreciated that the above compositions suitable for use with dental appliances are not exclusive. Those of skill in the art will be aware that some of the materials can be substituted or additional materials may be added without altering the key properties of the alloys of the current invention. For example, it is well known that small amounts of cobalt and palladium can be substituted with copper, nickel and iron. Alternatively, small concentrations (less than 5 wt. %) of these materials may also be added or be found in the alloy as impurities without affecting the properties of the overall composition.

To prove the utility of these alloys for dental products, exemplar compositions were successfully bonded to several popular dental porcelains. The inventors have fully tested the utility of the materials for dental applications by fabricating both single crowns and bridgework. In addition, they have shown that alloys in accordance with the invention can be processed using standard foundry processing techniques for cobalt alloys, indicating that the alloys of the invention will be useable with typical mass production casting and/or molding techniques.

Finally, biological testing has been completed on ruthenium containing alloys in the past and has determined alloys of this type to be non-cytotoxic. Although similar cytotoxicity tests have not been completed for the alloys of the current invention, ion release tests have been conducted for exemplary alloys, as shown in Table 3. The results show that the alloys of the current invention have very low ion release when subjected to immersion tests of the ISO standard. These low ion release rates suggest that not only will the alloys of the current invention be non-cytotoxic, but that they also possess very high electrochemical resistance, which is important in the oral environment.

Although the above description has focused on a range of compositions for the alloys of the current invention, the invention is also directed to a method of manufacturing a dental product generally comprising the steps of providing an alloy having a composition in accordance with the above description and then shaping that alloy using any suitable means. As discussed above, the alloy of the instant invention allows for the use of a number of conventional shaping techniques, such as, casting and molding. Moreover, the alloys of the current invention also allow for the use of more recent advances in shaping technologies, such as, for example, selective laser sintering. It should be understood that any of these techniques or a combination thereof may be used with the alloys of the current invention.

Those skilled in the art will appreciate that the foregoing examples and descriptions of various preferred embodiments of the present invention are merely illustrative of the invention as a whole, and that variations in the relative composition of the various components of the present invention may be made within the spirit and scope of the invention. For example, it will be clear to one skilled in the art that typical impurities and/or additives may be included in the compositions discussed above that would not affect the improved properties of the alloys of the current invention nor render the alloys unsuitable for their intended purpose. Accordingly, the present invention is not limited to the specific embodiments described herein but, rather, is defined by the scope of the appended claims.

What is claimed is:

1. A non-magnetic cobalt based dental alloy comprising:
   at least 30 wt. % Co;
   at least 25 wt. % Pd;
   at least 15 wt. % to 30 wt. % Cr; and
   at least one alloying material selected from the group consisting of molybdenum, tungsten, niobium, tantalum, vanadium and rhenium;
   wherein the concentration of the at least one alloying material is dependent on the concentration of Cr in accordance with the following:
      where Cr is at least 20 wt. % then the at least one alloying material is from 0 to 20 wt. %, and where Cr is less than 20 wt. % then the sum of Cr and the at least one alloying material is greater than 20 wt. %; and
   wherein the alloy is non-magnetic.

2. The non-magnetic cobalt based dental alloy of claim 1, wherein the alloy further comprises up to about 5 wt. % of at least one additive material selected from the group consisting of aluminum, boron, cerium, gallium, germanium and silicon.

3. The non-magnetic cobalt based dental alloy of claim 2, wherein the at least one additive material is selected from the group consisting of up to 2 wt. % gallium, up to 3 wt. % silicon, up to 1 wt. % boron, up to 3 wt. % aluminum, up to 3 wt. % germanium, and up to 1 wt. % cerium.

4. The non-magnetic cobalt based dental alloy of claim 1, wherein the alloy further comprises less than 5 wt. % of at least one trace additive selected from the group consisting of copper, nickel and iron.

5. The non-magnetic cobalt based dental alloy of claim 1, wherein the sum of Cr, Pd and the alloying material ranges from 45 wt. % to 70 wt. %.

6. The non-magnetic cobalt based dental alloy of claim 1, wherein the alloy composition comprises 44.75 wt. % cobalt, 20 wt. % chromium, 25 wt. % palladium, 10% molybdenum and 0.25 wt. % boron.

7. The non-magnetic cobalt based dental alloy of claim 1, wherein the alloy has a thermal expansion coefficient within the range of from about 13 to about $18 \times 10^{-6}$.

8. The non-magnetic cobalt based dental alloy of claim 1, wherein the alloy has a liquidus temperature of below about 1350° C.

9. A dental product comprising:
   a body for dental application, said body being formed of a non-magnetic cobalt based dental alloy comprising:
      at least 30 wt. % Co;
      at least 25 wt. % Pd;
      at least 15 wt. % to 30 wt. % Cr: and
      at least one alloying material selected from the group consisting of molybdenum. tungsten, niobium, tantalum, vanadium and rhenium;
      wherein the concentration of the at least one alloying material is dependent on the concentration of Cr in accordance with the following:
         where Cr is at least 20 wt. % then the at least one alloying material is from 0 to 20 wt. %, and where Cr is less than 20 wt. % then the sum of Cr and the at least one alloying material is greater than 20 wt. %; and
      wherein the alloy is non-magnetic.

10. The dental product of claim 9, wherein the alloy further comprises up to about 5 wt. % of at least one additive material selected from the group consisting of aluminum, boron, cerium, gallium, germanium and silicon.

11. The dental product of claim 10, wherein the at least one additive material is selected from the group consisting of up to 2 wt. % gallium, up to 3 wt. % silicon, up to 1 wt. % boron, up to 3 wt. % aluminum, up to 3 wt. % germanium, and up to 1 wt. % cerium.

12. The dental product of claim 9, wherein the alloy further comprises less than 5 wt. % of at least one trace additive selected from the group consisting of copper, nickel and iron.

13. The dental product of claim 9, where the sum of Pd. Cr and the alloying material ranges from 45 wt. % to 70 wt. %.

14. The dental product of claim 9, wherein the alloy comprises 44.75 wt. % cobalt, 20 wt. % chromium, 25 wt. % palladium, 10% molybdenum and 0.25 wt. % boron.

15. The dental product of claim 9, wherein the alloy has a thermal expansion coefficient of from about 13 to about $18 \times 10^{-6}$.

16. The dental product of claim 9, wherein the alloy has a liquidus temperature of below about 1350° C.

* * * * *

UNITED STATES PATENT AND TRADEMARK OFFICE
CERTIFICATE OF CORRECTION

PATENT NO. : 8,623,272 B2
APPLICATION NO. : 12/050006
DATED : January 7, 2014
INVENTOR(S) : Prasad et al.

Page 1 of 1

It is certified that error appears in the above-identified patent and that said Letters Patent is hereby corrected as shown below:

In the Claims:

In column 8 at line 51, In Claim 9, change "molybdenum." to --molybdenum,--.

In column 9 at line 7, In Claim 13, change "Pd." to --Pd,--.

Signed and Sealed this
Fifteenth Day of July, 2014

Michelle K. Lee
*Deputy Director of the United States Patent and Trademark Office*